United States Patent
Tu et al.

(10) Patent No.: US 11,064,897 B2
(45) Date of Patent: *Jul. 20, 2021

(54) METHOD AND SYSTEM FOR CALCULATING BLOOD VESSEL PRESSURE DIFFERENCE AND FRACTIONAL FLOW RESERVE

(71) Applicant: PULSE MEDICAL IMAGING TECHNOLOGY (SHANGHAI) CO., LTD, Shanghai (CN)

(72) Inventors: Shengxian Tu, Shanghai (CN); Miao Chu, Shanghai (CN); Bing Liu, Shanghai (CN); Yazhu Chen, Shanghai (CN)

(73) Assignee: PULSE MEDICAL IMAGING TECHNOLOGY (SHANGHAI) CO., LTD, Shanghai (CN)

( * ) Notice: Subject to any disclaimer, the term of this patent is extended or adjusted under 35 U.S.C. 154(b) by 362 days.

This patent is subject to a terminal disclaimer.

(21) Appl. No.: 15/777,817

(22) PCT Filed: Nov. 4, 2016

(86) PCT No.: PCT/CN2016/104618
§ 371 (c)(1),
(2) Date: May 21, 2018

(87) PCT Pub. No.: WO2017/097073
PCT Pub. Date: Jun. 15, 2017

(65) Prior Publication Data
US 2018/0344173 A1    Dec. 6, 2018

(30) Foreign Application Priority Data
Dec. 8, 2015  (CN) .......................... 201510901329.X

(51) Int. Cl.
*A61B 5/026* (2006.01)
*A61B 5/02* (2006.01)
(Continued)

(52) U.S. Cl.
CPC .......... *A61B 5/026* (2013.01); *A61B 5/02007* (2013.01); *A61B 5/02158* (2013.01);
(Continued)

(58) Field of Classification Search
CPC ..... A61B 5/026; A61B 5/7275; A61B 5/7282; A61B 5/02007; A61B 5/02158;
(Continued)

(56) References Cited

U.S. PATENT DOCUMENTS 9,891,044 B2 *   2/2018  Tu ........................... A61B 5/021
10,617,473 B2 *   4/2020  Tu ............................ A61B 8/04
(Continued)

FOREIGN PATENT DOCUMENTS

CN       102905614 A       1/2013
CN       103300820 A       9/2013
(Continued)

OTHER PUBLICATIONS

Tar et al., "The Effect of the Sensor Position of the Pressure Wire Distal to a Coronary Stenosis on the Calculated Fractional Flow Reserve", Computing in Cardiology, 2013, pp. 1099-1102, col. 40.

*Primary Examiner* — Serkan Akar
*Assistant Examiner* — Renee C Langhals
(74) *Attorney, Agent, or Firm* — Muncy, Geissler, Olds & Lowe, P.C.

(57) ABSTRACT

A method for computing fractional flow reserve (FFR), including receiving geometrical parameters of a blood vessel segment including a proximal end and a distal end, the geometrical parameters including a first geometrical parameter, a second geometrical parameter and a third geometrical (Continued)

parameter; and with the proximal end as a reference point, deriving a reference lumen diameter function and a geometrical parameter difference function based on the geometrical parameters and the distance from the position along the segment of blood vessel to the reference point. Derivatives of the geometrical parameter difference function are calculated in multiple scales. FFR is computed as a ratio of a second blood flow pressure at the first location of the blood vessel to a first blood flow pressure at the proximal end of the segment based on the multiple scales of derivative difference functions and the maximum mean blood flow velocity.

11 Claims, 2 Drawing Sheets

(51) Int. Cl.
  *A61B 5/0215* (2006.01)
  *A61B 5/00* (2006.01)
  *G16H 50/20* (2018.01)
  *A61B 6/00* (2006.01)

(52) U.S. Cl.
  CPC .......... *A61B 5/6852* (2013.01); *A61B 5/7275* (2013.01); *A61B 5/7282* (2013.01); *G16H 50/20* (2018.01); *A61B 5/0073* (2013.01); *A61B 5/7264* (2013.01); *A61B 6/504* (2013.01); *A61B 6/5217* (2013.01); *A61B 2505/01* (2013.01); *A61B 2576/023* (2013.01)

(58) Field of Classification Search
  CPC . A61B 5/6852; A61B 2505/01; A61B 5/7264; A61B 2576/023; A61B 5/0073; A61B 6/504; A61B 6/5217; A61B 5/021; G16H 50/20
  USPC ......................................................... 600/407
  See application file for complete search history.

(56) References Cited

U.S. PATENT DOCUMENTS

| | | | |
|---|---|---|---|
| 2013/0028494 A1* | 1/2013 | Groth | .................. G06T 7/0012 382/130 |
| 2014/0073976 A1 | 3/2014 | Fonte et al. | |
| 2015/0238121 A1 | 8/2015 | Tu et al. | |
| 2015/0268039 A1 | 9/2015 | Tu et al. | |

FOREIGN PATENT DOCUMENTS

| | | |
|---|---|---|
| CN | 103829933 A | 6/2014 |
| CN | 103932694 A | 7/2014 |
| CN | 104768465 A | 7/2015 |
| CN | 105326486 A | 2/2016 |
| EP | 2544585 B1 | 1/2013 |
| NL | 2012324 | 9/2015 |
| WO | WO 2010/033971 A1 | 3/2010 |
| WO | WO-2010033971 A1 | 3/2010 |

* cited by examiner

METHOD AND SYSTEM FOR CALCULATING BLOOD VESSEL PRESSURE DIFFERENCE AND FRACTIONAL FLOW RESERVE

TECHNICAL FIELD

The present invention relates to the field of medical treatment and, in particular, to image-based computational methods and systems for use in acquisition of a pressure drop and fractional flow reserve (FFR) within a blood vessel.

BACKGROUND

Plaque-induced stenosis of a blood vessel can pose a health threat because it hampers myocardial blood supply. Although coronary angiography can reveal the severity of coronary stenosis, it is incapable of reflecting functional significances of stenosis. Fractional flow reserve (FFR) generally refers to myocardial FFR, defined as the ratio of a maximum volumetric flow rate that a stenotic coronary artery can provide for myocardium to a maximum volumetric flow rate if that same artery were to be normal. This ratio can be obtained based on the ratio of the pressure distal to a stenosis relative to the pressure proximal to the stenosis during the maximal coronary blood flow (hyperemia).

FFR is used to evaluate the physiological function of a diseased blood vessel, allowing lesion-specific diagnosis of coronary artery, and is in close relation to prognosis outcomes. When coronary angiography is ambiguous to determine whether a blood vessel of interest is associated with myocardial ischemia, FFR can provide direct information that is helpful in diagnosis and decision-making. A good prognosis can be expected from FFR-based decision-making. In general, FFR≤0.80 is taken as an indication of a need for vascular reconstruction, while FFR>0.80 is considered that there is no such a need for the moment. This simple principle can apply even to complex lesions. FFR may be of even higher value in the era of stenting when interventional physicians are faced with more complex lesions.

For critical coronary lesions, while coronary angiography can reveal the severity degree of coronary stenosis, it has limited ability in accurate evaluation of ischemia. So far, a number of studies have confirmed that FFR can serve as a robust criterion for coronary functional assessment.

Pressure may be invasively measured by a wire with pressure sensor. Such intervention, however, involves a significant amount of work and is associated with a risk of damaging the vessel. A geometrical model of a coronary artery tree can be built using three-dimensional or two-dimensional quantitative coronary angiography. However, computational fluid dynamic analysis of a geometrical model of a reconstructed coronary system involves a great amount of computation to solve complex fluid dynamic equations. There are also some methods in which the length and degree of stenosis are presumed to be constant, which, however, may lead to inaccurate results, in particular in the diffuse intermediate stenosis because of the subjectivity in determining the length and degree of stenosis.

Existing methods for computing pressure drop based on coronary geometrical parameters (e.g., coronary diameter or cross-sectional area) are incapable of properly distinguishing and evaluating the different impacts of geometric changes of a stenosed vessel with different degrees of severity on the blood flow pressure. Several typical conventional methods for FFR computation are briefed below.

CN103932694A (Reference 1) discloses a method for accurate myocardial FFR diagnosis. At first, patients with FFR>0.8 or <0.6 are precluded by means of "noninvasive (CT+ultrasound) FFR diagnosis". The remaining patients (0.6≤FFR≤0.8) are then subjected to accurate interventional measurement of coronary stenosis using an "FFR diagnosis system" to determine FFR value. In the "noninvasive (CT+ultrasound) FFR diagnosis", the epicardial coronary artery tree of each patient is geometrically modeled by a program for FFR computation based on morphological parameters determined by a CT reconstruction program. As taught in Reference 1, the patient's FFR is computed using an FFR analysis which involves: computing the aortic pressure at maximal coronary hyperemia, a theoretic resistance of the epicardial coronary artery tree deduced from Bernoulli's equation and the outlet resistance at maximal coronary hyperemia; firstly, computing the blood flows and pressures of each vessel, then computing a new resistance of the epicardial coronary artery tree based on the resulting blood flows of each vessel; and recalculating the blood flows and inlet and outlet pressures of each vessel. These steps are repeated until both a relative velocity error and a relative pressure error between successive repetitions become <$10^{-4}$, following by calculation of FFR based on a predetermined equation.

CN102905614A (Reference 2) discloses a method for interventional measurement of a stenosis in a vessel, including: taking a succession of pressure measurements and a succession of velocity measurements at each of first and second locations that are both within the vessel and different from a target location within the vessel using a pressure sensor (e.g., a pressure guide wire) and a velocity sensor deployed at the different locations within the vessel; determining a wave speed in the fluid medium based on the square of a change in pressure divided by the square of a change in velocity; computing forward pressure changes for the first and second locations; and subject pressure changes to integral summation and obtaining FFR from a ratio between the integral summation results.

CN103829933A (Reference 3) discloses a method for interventional detection of a stenosis of a blood vessel, comprising: interventional deployment of two pressure sensors (pressure sensor 1 and pressure sensor 2) in the vessel; taking readings of the pressure sensors; determining whether there is a stenosis between the two pressure sensors based on a pressure deviation indicated in the readings of these sensors. If the pressure deviation is less than a predefined threshold K, it is considered there is no stenosis, and vice versa. Alternatively, the measurements of the pressure sensors may be provided to the physician as a reference for diagnosis.

US20150268039A1 (Reference 4) discloses a method for determining a pressure drop in a segment of a blood vessel, comprising: receiving geometry data on different geometrical ends of the vessel, the geometrical ends including a proximal end and a distal end, the geometry data including a first geometrical parameter indicative of a first cross-sectional area at the distal end of the blood vessel, a second geometrical parameter indicative of a second cross-sectional area at the proximal end of the blood vessel and a third geometrical parameter indicative of a cross-sectional area at a first location between the proximal end and the distal end; receiving data indicative of a fluid flow velocity through the segment; determining a reference geometrical parameter value at the first location based on the first, second and third geometrical parameters and location data related to the first location; and determining a pressure deviation between a first fluid pressure at the distal end and a second fluid pressure at the first location based on the reference geometrical parameter value at the first location, the third geometrical parameter and the fluid flow velocity.

WO2010033971A1 (Reference 5) discloses a method for determining FFR, comprising: positioning a device comprising at least two sensors within a lumen at or near a stenosis, wherein the at least two sensors are separated by a predetermined distance L from one another; detecting a first parameter value of a first parameter of a first fluid within the lumen using at least one of the at least two sensors; injecting a second fluid into the lumen, wherein the second fluid is considered to temporarily displace the first fluid at the site of injection; and recording a second parameter value of a second parameter of the second fluid by the at least two sensors separated by the known distance. The first parameter and the second parameter may be pH, temperature, conductivity of the fluids. The first parameter value is different from the second parameter value in magnitude. The time interval T between times when the second parameter value is detected by the two sensors is recorded, and a mean velocity of the second fluid is calculated based on the distance L and the time interval T. Further, FFR is determined based on cross-sectional areas of the lumen at, proximal to and distal from the stenosis as well as on a mean aortic pressure.

Tu Shengxian et al. (Reference 6) proposed a new computer model for FFR computation. A geometrical model of a blood vessel was first built with three-dimensional (3D) quantitative coronary angiography (QCA). A mean volumetric flow rate at hyperemia was calculated using TIMI frame count combined with 3D QCA. The mean volumetric flow rate at hyperemia and a mean blood flow pressure measured using a catheter were used as inlet boundary conditions for computational fluid dynamics simulation, and FFR was obtained from fluid dynamic equations.

Taylor et al. (Reference 7) developed a non-invasive FFR computation method through applying computational fluid dynamics in coronary computed tomography angiography (CTA). Based on anatomic data obtained from CTA including the volume and mass of myocardium supplied by a vessel, a maximal coronary blood flow was estimated and the downstream microcirculatory resistance of the vessel was simulated as boundary conditions for computational fluid dynamics. FFR was then obtained by solving fluid dynamic equations.

Although these References present different methods for determining a pressure drop within a blood vessel from different points of view, they are each associated with at least one of the following deficiencies: (1) interventional acquisition of geometrical parameters of a blood vessel with a pressure wire is expensive and leads to physical damage to patients; (2) although computation of a pressure drop in a single scale is suitable for the cases of regular vascular stenosis, it could not properly distinguish and evaluate different impacts of changes in geometrical parameters of a stenosed vessel with different degrees of severity (e.g., a blood vessel with both focal and diffuse lesions) on blood flow pressure; (3) computational fluid dynamic (CFD) analysis of a geometrical model built with coronary angiography or CT reconstruction is complex, requires a huge amount of computation and consumes a great amount of time; (4) manual assessment of the severity (e.g. length) of a lesion, especially a diffuse lesion, is greatly subjective and tends to cause errors; (5) computation of a blood flow velocity requires maximal coronary hyperemia induced by adenosine which involves a complex operation and increases the patient's pain; and (6) three-dimensional reconstruction of all side branches of the stenosed vessel is required which is labor intensive.

Therefore, there is a need for a novel method for computing pressure drop in a blood vessel, which overcomes some or all of the above deficiencies and allows fast and accurate FFR computation.

SUMMARY OF THE INVENTION

The object of the present invention is to provide a novel method for computation of pressure drop within a segment of blood vessel and FFR. The present invention comprises: receiving geometrical parameters of a blood vessel segment having a proximal end and a distal end, the geometrical parameters comprising a first geometrical parameter representing a cross-sectional area or diameter of the blood vessel segment at the proximal end, a second geometrical parameter representing a cross-sectional area or diameter of the blood vessel segment at the distal end, and a third geometrical parameter representing a cross-sectional area or diameter of the blood vessel segment at a first location between the proximal end and the distal end; receiving a mean blood velocity within the segment; computing a reference lumen diameter at the first location of the segment based on the first, second and third geometrical parameter and location data related to the first location; computing a geometrical parameter difference at the first location based on the difference between the third geometrical parameter and the reference lumen diameter; based on the geometrical parameter difference, the mean blood flow velocity V and its square $V^2$, a pressure deviation $\Delta P$ between a first blood flow pressure at the proximal end and a second blood flow pressure at the first location is determined.

Preferably, the method may further comprise: with the proximal end as a reference point, deriving a reference lumen diameter function based on the first geometrical parameter, the second geometrical parameter and a distance x from a certain point along the segment of vessel to the reference point, wherein the reference lumen diameter function is used to represent reference lumen diameter at different positions along the blood vessel as a function of the distance x from the position to the reference point. Preferably, the derivation of the reference lumen diameter function comprises a linear normalization as a function of location from proximal end to distal end of the vessel segment.

Preferably, the method may further comprise: with the proximal end as a reference point, deriving a geometrical parameter difference function based on the third geometrical parameter and the reference lumen diameter function, wherein the geometrical parameter difference function indicates differences between the reference lumen diameter function and the received geometrical parameters with respect to the distances x from the reference point.

Preferably, the method may further comprise: computing derivatives of the geometrical parameter difference function in multiple scales, and wherein the pressure deviation $\Delta P$ between the first blood flow pressure and the second blood flow pressure is computed based on the multiple scales of derivative difference functions. The scales are resolutions, including a first greater scale and a second smaller scale, indicative of distances between two adjacent points when calculating derivative numerically. The multiple scales of derivative difference functions comprise a derivative difference function $f_1(x)$ in the first scale and a derivative difference function $f_2(x)$ in the second scale, wherein multiple scales enables manifestation of impacts of different severity of stenosis (focal and diffuse) on the pressure deviation, wherein the first scale of derivative difference function $f_1(x)$ is adapted to detect a geometrical parameter difference caused by long sever lesion ignoring focal stenosis and wherein the second scale of derivative difference function $f_2(x)$ is adapted to detect a geometrical parameter difference caused by a focal lesion.

Preferably, the method may further comprise: computing the pressure deviation $\Delta P$ between the first blood flow pressure and the second blood flow pressure by weighting integrals of the first scale of derivative difference function $f_1(x)$ and the second scale of derivative difference function $f_2(x)$ as well as the mean blood flow velocity V and its square $V^2$.

Preferably, the method may further comprise: computing the pressure deviation $\Delta P$ between the first blood flow pressure and the second blood flow pressure according to $$\Delta P = \alpha [C_1 V + C_2 V^2] * \int f_1(x)dx + \beta [C_1 V + C_2 V^2] * \int f_2(x)dx$$

where $C_1$ and $C_2$ represent coefficients of the mean blood flow velocity V and its square $V^2$, respectively, and $\alpha$ and $\beta$ denote weighting coefficients for the derivative difference functions in the first and second scales, respectively.

Preferably, the method may further comprise: computing derivatives of the geometrical parameter difference function in n scales, wherein the pressure deviation $\Delta P$ between the first blood flow pressure and the second blood flow pressure is computed based on the n scales of derivatives, wherein the scales are resolutions indicative of distanced between two adjacent points when calculating derivative numerically, wherein the n scales consist of a first scale, a second scale, . . . , and an n-th scale, wherein the first scale of derivative difference function $f_1(x)$ is adapted to detect a geometrical parameter difference between an actual lumen diameter and a reference lumen diameter caused by a first lesion characteristic, ignoring other lesion characteristics, and the second scale of derivative difference function $f_2(x)$ is adapted to detect a geometrical parameter difference caused by a second lesion characteristic, . . . , wherein the n-th scale of derivative difference function $f_n(x)$ is adapted to detect a geometrical parameter difference caused by an n-th lesion characteristic, and wherein n is a natural number greater than 1.

Preferably, the method may further comprise: computing the pressure deviation $\Delta P$ between the first blood flow pressure and the second blood flow pressure by weighting integrals of the derivative difference function $f_1(x)$, . . . , $f_n(x)$ in the n scales as well as the mean blood flow velocity V and its square $V^2$.

Preferably, the method may further comprise: computing the pressure deviation $\Delta P$ between the first blood flow pressure and the second blood flow pressure according to $$\Delta P = \alpha_1 [C_1 V + C_2 V^2] * \int f_1(x)dx + \alpha_2 [C_1 V + C_2 V^2]$$
$$\int f_2(x)dx + \ldots + \alpha_n [C_1 V + C_2 V^2] * \int f_n(x)dx$$

where, $C_1$ and $C_2$ represent coefficients of the mean blood flow velocity V and its square $V^2$, respectively, and $\alpha_1, \alpha_2, \ldots,$ and $\alpha_n$ denote weighting coefficients for the derivative difference functions $f_1(x), f_2(x), \ldots, f_n(x)$ in the n scales, respectively.

Preferably, the location data related to the first location is the distance from the first location to the proximal end of the segment, and the mean blood flow velocity of the segment is the mean velocity from the proximal to the distal end.

Preferably, the method may further comprise: receiving two-dimensional coronary angiography images under a certain angle; and images registration is performed on the regions of interest for different frames, wherein the region of interest of the coronary angiography is from the proximal end of the vessel segment to the distal end.

Preferably, the method may further comprise: plotting gray-level histograms for the registered region of interest; and calculating the gray-level fitting function with respect to time changes within a cardiac cycle.

Preferably, the method may further comprise: obtaining a mean flow velocity of contrast medium within the segment of vessel based on the gray-level fitting function.

Preferably, the mean blood flow velocity V within the segment of vessel is approximately equal to the mean contrast medium velocity obtained from the gray-level fitting function.

The present invention also provides a method for computing fractional flow reserve (FFR) of a vessel segment, comprising: receiving patient's mean blood flow velocity V of the vessel segment in a resting state, which could be optionally obtained by conventional angiography (without maximum microcirculation dilation); calculating a maximum blood flow velocity $V_{max}$ under a maximum dilation of microcirculation based on the mean velocity V; solving for a pressure deviation $\Delta P_{max}$ corresponding to the maximum blood flow velocity; and obtaining FFR according to FFR= $(P1 - \Delta P_{max})/P1$, where P1 represents a first blood flow pressure at the proximal end of the segment, which can be approximately estimated by cardiac diastolic and systolic pressures or accurately measured using a catheter.

Preferably, the method may further comprise: obtaining the maximum blood flow velocity by looking up a correspondence table listing mean coronary blood flow velocities under a resting state and the corresponding maximum blood flow velocities under the condition of maximum dilation of microcirculation.

Preferably, the method may further comprise: obtaining a pressure deviation $\Delta P_{max}$ across the segment corresponding to the maximum blood flow velocity using the method as defined above.

Preferably, FFR may be solved for a given fixed maximum blood flow velocity $V_{max}$.

The present invention also provides a method of computing fractional flow reserve (FFR) of a blood vessel segment, comprising: receiving geometry parameters of a blood vessel segment having a proximal end and a distal end, the geometrical parameters comprising a first geometrical parameter representing a cross-sectional area (or diameter) of the blood vessel segment at the proximal end, a second geometrical parameter representing a cross-sectional area (or diameter) of the blood vessel segment at the distal end, and a third geometrical parameter representing a cross-sectional area (or diameter) of the blood vessel segment at a first location between the proximal end and the distal end; with the proximal end as a reference point, deriving a reference lumen diameter function and a geometrical parameter difference function based on the geometrical parameters with respect to the distance from the position along the segment of the vessel to the reference point; obtaining derivatives of the geometrical parameter difference function in multiple scales, wherein the scales are resolutions indicative of distanced between two adjacent points when calculating derivative numerically; receiving a mean blood flow velocity of the blood vessel segment through conventional coronary angiography and obtaining a maximum mean blood flow velocity of the blood vessel segment by looking up a table; and computing FFR as a ratio of a second blood flow pressure at the first location of the blood vessel to a first blood flow pressure at the proximal end, based on the multiple scales of derivative difference functions and the maximum mean blood flow velocity.

The present invention also provides a system for computing a pressure deviation in a blood vessel segment, which is able to implement the method as defined above, the system comprising: a geometrical parameter data acquisition module, configured to acquire geometrical parameters of a blood vessel segment, the blood vessel segment comprising a proximal end and a distal end, the geometrical parameters comprising a first geometrical parameter representing a cross-sectional area or diameter of the blood vessel segment at the proximal end, a second geometrical parameter representing a cross-sectional area or diameter of the segment at the distal end, and a third geometrical parameter representing a cross-sectional area or diameter of the blood vessel segment at a first location between the proximal end and the distal end; a location data acquisition module, configured to acquire location data related to the first location; a velocity acquisition module, configured to acquire a mean blood flow velocity of the blood vessel segment and the square of the mean blood flow velocity; a reference lumen diameter computation module, configured to compute a reference lumen diameter at the first location of the blood vessel segment based on the first geometrical parameter, the second geometrical parameter, the third geometrical parameter and the location data related to the first location; a geometrical parameter difference computation module, configured to compute a geometrical parameter difference between the third geometrical parameter and the reference lumen diameter at the first location; and a pressure deviation computation module, configured to receive the geometrical parameter difference data at the first location output from the geometrical parameter difference computation module and the mean blood flow velocity and its square from the velocity acquisition module and then to compute the pressure deviation $\Delta P$ between a first blood flow pressure at the proximal end and a second blood flow pressure at the first location.

Preferably, the reference lumen diameter computation module may be configured to derive a reference lumen diameter function, based on the first geometrical parameter, the second geometrical parameter and a distance x from a certain position along the segment of vessel to the proximal end as a reference point, wherein the reference lumen diameter function is used to represent reference lumen diameter along different positions along the blood vessel as a function of the distance x between the position and the reference point, wherein the system preferably further comprises a normalization module configured to perform a linear normalization as a function of location from the proximal end to the distal end of the vessel segment.

Preferably, the geometrical parameter difference computation module may be configured to derive a geometrical parameter difference function, based on the third geometrical parameter and a reference lumen diameter function with the proximal end point as a reference point. The geometrical parameter difference function indicates a relationship of differences between the reference lumen diameter function and the received geometrical parameters with respect to the distances x from the reference point.

Preferably, the system may further comprise a multi-scale derivative difference computation module configured to obtain the derivations of the geometrical parameter difference function in multiple scales, wherein the pressure deviation computation module computes the pressure deviation $\Delta P$ between the first blood flow pressure and the second blood flow pressure by weighting integrals of the derivative difference functions in multiple scales based on the output of the multi-scale difference derivative computation module as well as the mean blood flow velocity V and its square $V^2$ output from the velocity acquisition module, and wherein the multiple scales comprise two or more scales implemented as resolutions indicative distances between two adjacent points when calculating derivative numerically.

Preferably, the system may further comprise a two-dimensional coronary angiography module configured to capture two-dimensional coronary angiography under a certain angle and register region of interest of the images for different frame counts, wherein region of interest of the coronary angiography is from the proximal end of the vessel segment to the distal end.

Preferably, the velocity acquisition module may be configured to plot a gray-level histogram for the registered region of interest based on the output from the two-dimensional coronary angiography module, and fit it as a function of time within a cardiac cycle, from which a mean flow velocity of the contrast medium was obtained.

The present invention also provides a system for computing fractional flow reserve (FFR) of a blood vessel segment, comprising: a geometrical parameter data acquisition module, configured to acquire geometrical parameters of the blood vessel segment, which comprise a proximal end and a distal end. The geometrical parameters comprise a first geometrical parameter representing a cross-sectional area (or diameter) of the proximal end of the segment, a second geometrical parameter representing a cross-sectional area (or diameter) of the distal end of the segment, and a third geometrical parameter representing a cross-sectional area (or diameter) of the blood vessel segment at a first location between the proximal end and the distal end; a location data acquisition module, configured to acquire location data related to the first location; a reference lumen diameter computation module, configured to derive a reference lumen diameter function with respect to the distance x from a certain position along the blood vessel segment to the proximal end as a reference point; a geometrical parameter difference computation module, configured to derive a parameter difference function based on the reference lumen diameter function and the third geometrical parameter; a multi-scale computation module, configured to obtain derivatives of the geometrical parameter difference function in multiple scales implemented as resolutions indicative of distances between two adjacent points when calculating derivative numerically; a mean blood flow velocity acquisition module, configured to acquire a mean blood flow velocity of the segment through conventional coronary angiography; a maximum mean blood flow velocity computation module, configured to obtain a maximum mean blood flow velocity of the blood vessel segment by looking up a correspondence table stored in the module; and an FFR computation module, configured to obtain FFR as ratio of a second blood flow pressure at the first location of the blood vessel to a first blood flow pressure at the proximal end, based on the multiple scales of derivative difference functions and the maximum mean blood flow velocity.

In a specific embodiment, the present invention also provides a system for computing fractional flow reserve (FFR) of a blood vessel segment, comprising: a mean blood flow velocity acquisition module, configured to acquire a mean blood flow velocity V of the segment preferably by coronary angiography (without maximum dilation of microcirculation); a maximum blood flow velocity acquisition module, configured to calculate a maximum blood flow velocity $V_{max}$ under the condition of maximum dilation of microcirculation based on the mean velocity V; a pressure deviation computation module, configured to solve for a pressure deviation $\Delta P_{max}$ corresponding to the maximum blood flow velocity; and an FFR computation module, configured to obtain FFR, based on a first blood flow pressure P1 at the proximal end of the segment and the pressure deviation $\Delta P_{max}$, according to FFR=(P1−$\Delta$Pmax)/P1, wherein P1 can be approximately estimated from cardiac diastolic and systolic pressures or accurately measured using a catheter.

Preferably, the maximum blood flow velocity acquisition module may be configured to obtain the maximum blood flow velocity by looking up a correspondence table listing mean coronary blood flow velocities in a resting state and the corresponding maximum blood flow velocities under the condition of maximum dilation of microcirculation, and the correspondence table could be stored in the maximum blood flow velocity acquisition module or another separate storing module of the system.

The present invention offers the following benefits: it provides a novel method for computing a pressure drop within a blood vessel, which achieves feasibility and operability for fast and accurate FFR calculation, and a novel method for obtaining a maximum mean blood flow velocity, which allows for an easy and convenient operation. In addition, computation in the multiple scales allows obtaining the pressure drop within the stenosed vessel with different degrees of severity (e.g., focal and diffuse lesions).

DETAILED DESCRIPTION

Figure 1:
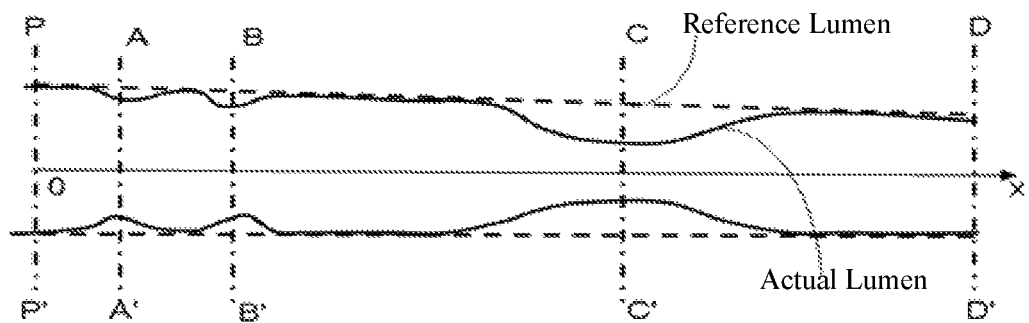
FIG. 1 schematically illustrates a structural comparison between a stenosed lumen and its reference lumen of the present invention.

Technical solutions according to embodiments of the present invention will be thoroughly described below with reference to the accompanying drawings so that they will be clearer. Apparently, the embodiments set forth below are only some, but not all embodiments of the inventions. All other embodiments obtained by those of ordinary skill in the art based on the embodiments disclosed herein fall within the scope of the invention.

Embodiment 1

The present invention provides a method for computing a pressure deviation within a segment of a blood vessel, the method comprising: receiving geometrical parameters of the segment having a proximal end point and a distal end point. The geometrical parameters include: a first geometrical parameter representing a cross-sectional area (or diameter) of the segment at the proximal end; a second geometrical parameter representing a cross-sectional area (or diameter) of the segment at the distal end; and a third geometrical parameter representing a cross-sectional area (or diameter) of the first location at a first location between the proximal end point and the distal end point. Based on the first geometrical parameter, the second geometrical parameter, the third geometrical parameter and location data related to the first location, a reference (assuming there was no lesion) lumen diameter of the blood vessel at the first location can be obtained. A geometrical parameter difference between an actual lumen diameter and the reference lumen diameter at the first location is calculated based on the third geometrical parameter and the reference lumen diameter at the first location. Preferably, the geometrical parameter difference is obtained from the division of the actual lumen diameter by the reference lumen diameter.

With the proximal end point as a reference point, based on the first geometrical parameter, the second geometrical parameter and the distance x of a certain position on the segment from the reference point, a reference lumen diameter function is derived, which represents reference lumen diameter at different positions along the blood vessel as a function of the distance x from the position to the reference point. Based on the third geometrical parameter and the reference lumen diameter function, a geometrical parameter difference function is derived, which represents the variation of a difference between the reference lumen diameter function and the received geometrical parameters with respect to the distance x from the reference point.

In a specific embodiment, the derivation of the reference lumen diameter function includes linear normalization of location parameters in the range from the proximal end of the segment to the distal end.

In a specific embodiment, with the proximal end as a reference point, based on the third geometrical parameter and the reference lumen diameter function, a geometrical parameter difference function is derived, which represents a variation of a difference between the reference lumen diameter function and the received geometrical parameters with the distance x from the reference point.

In a specific embodiment, multiple scales of derivative difference functions of the geometrical parameter difference are derived, based on which a pressure deviation $\Delta P$ between a first blood flow pressure and a second blood flow pressure is calculated.

Wherein, the scales are resolutions indicative of distances between two adjacent points when calculating the derivative numerically. The multiple scales include a first greater scale and a second smaller scale. Use of the multiple scales allows manifestation of the impacts of different degrees of stenosis (focal and diffuse) on the blood flow pressure deviation.

In a specific embodiment, the different scales include a first greater scale and a second smaller scale, and the multiple scales of derivative difference functions include a derivative difference function $f_1(x)$ in the first scale and a derivative difference function $f_2(x)$ in the second scale. Use of the different scales allows manifestation of impacts of different degrees of stenosis (focal and diffuse) on the blood flow pressure deviation. The first scale of derivative difference function $f_1(x)$ is adapted to detect a geometrical parameter difference between an actual lumen diameter and a reference lumen diameter caused by long sever lesion ignoring focal stenosis. The second scale of derivative difference function $f_2(x)$ is utilized to detect a geometrical parameter difference caused by a focal stenosis.

The pressure deviation $\Delta P$ between the first blood flow pressure and the second blood flow pressure can be obtained by weighting integrals of the first and the second scale of derivative difference function as well as a mean blood flow velocity V and its square $V^2$.

Preferably, the pressure deviation ΔP between the first blood flow pressure and the second blood flow pressure is obtained according to $$\Delta P = \alpha[C_1 V + C_2 V^2] * \textstyle\int f_1(x)dx + \beta[C_1 V + C_2 V^2] * \textstyle\int f_2(x)dx$$

where, $C_1$ and $C_2$ represent coefficients of the mean blood flow velocity V and its square $V^2$, respectively, and α and β denote weighting coefficients for the derivative difference functions in the first and second scales, respectively.

Preferably, in order to more accurately compute the pressure deviation within the segment of the vessel under various conditions, it could be contemplated to calculate derivatives of the geometrical parameter difference function in n different scales and calculate the pressure deviation between the first blood flow pressure and the second blood flow pressure based on the n scales of derivative difference functions. That is:

The derivatives of the geometrical parameter difference function in the n scales are derived, and the pressure deviation ΔP between the first blood flow pressure and the second blood flow pressure is calculated based on the n scales of derivative difference functions. The scales are implemented as resolutions indicative of distances between two adjacent points when calculating derivative numerically. The n scales are a first scale, a second scale, . . . , and an n-th scale.

The first scale of derivative difference function $f_1(x)$ is adapted to detect a geometrical parameter difference between an actual lumen diameter and a reference lumen diameter caused by a first lesion characteristic, with geometrical parameter differences attributed to other lesions being ignored.

The second scale of derivative difference function $f_2(x)$ is adapted to detect a geometrical parameter difference between an actual lumen diameter and a reference lumen diameter caused by a second lesion characteristic, . . . , and the derivative difference function $f_n(x)$ in the n-th scale is adapted to detect a geometrical parameter difference between an actual lumen diameter and a reference lumen diameter caused by an n-th lesion characteristic. n is a natural number greater than 1. The pressure deviation ΔP between the first blood flow pressure and the second blood flow pressure can be obtained by weighting integrals of the n scales of derivative difference functions $f_1(x)$, . . . , $f_n(x)$ as well as a mean blood flow velocity V and its square.

Preferably, the pressure deviation ΔP between the first blood flow pressure and the second blood flow pressure is obtained according to:

$$\Delta P = \alpha_1 [C_1 V + C_2 V^2] * \textstyle\int f_1(x)dx + \alpha_2 [C_1 V + C_2 V^2] \textstyle\int f_2(x)dx + \ldots + \alpha_n [C_1 V + C_2 V^2] * \textstyle\int f_n(x)dx$$

where, $C_1$ and $C_2$ represent coefficients of the mean blood flow velocity V and its square $V^2$, respectively, and $\alpha_1, \alpha_2, \ldots,$ and $\alpha_n$ denote weighting coefficients for the derivative difference functions $f_1(x), f_2(x), \ldots, f_n(x)$ in the n scales, respectively.

Preferably, the location data related to the first location indicate the distance from the first location to the proximal end of the segment, and the mean blood flow velocity of the segment is a mean velocity from the proximal end to the distal end.

Preferably, the method further includes: receiving two-dimensional coronary angiography images under a certain angle; and registering a region of interest of the images for different frames. The region of interest of the coronary angiography is from the proximal end to the distal end.

Preferably, the method further includes: plotting a gray-level histogram for the registered region of interest; and fitting the gray value as a function of time within a cardiac cycle.

Preferably, the method further includes: obtaining a mean flow velocity of the contrast medium within the segment of the vessel based on the gray-level fitting function.

Preferably, the mean blood flow velocity V of the segment is approximately equal to the mean contrast medium velocity obtained from the gray-level fitting function.

The method will be described in further detail below with reference to FIGS. 1 and 2. Referring to FIG. 1, the method includes: receiving geometrical parameters of a segment of a blood vessel, including: (a) a geometrical parameter (cross-sectional area or diameter) at a proximal end P of the segment; (b) a geometrical parameter (cross-sectional area or diameter) at a distal point D of the segment; and (c) taking P as a reference point, a geometrical parameter (cross-sectional area or diameter) of the segment between P and D as well as the distance x from the position of the segment to the reference point P are obtained.

The geometrical parameters may be obtained by any of a variety of techniques including two-dimensional or three-dimensional coronary angiography, coronary computed tomography angiography (CTA), intravascular ultrasound (IVUS) or optical coherence tomography (OCT). Generally, the geometrical parameters of the segment may be its cross-sectional areas or diameters. In case of two-dimensional diameters of the blood vessel being received, we can assume the cross-sections of the blood vessel to be circular and thus can obtain its cross-sectional areas.

Based on these data (a), (b) and (c), a reference geometrical parameter of the segment (assuming there was no lesion) can be obtained and represented as a linear function of the distance from the reference point P. In FIG. 1, the solid lines represents an actual lumen of the segment, while the dotted lines represents a reference lumen thereof. A geometrical parameter difference as a function of the distance from the reference point P can be derived from a ratio of the geometrical parameter of the reference lumen to that of the actual lumen.

Figure 2:
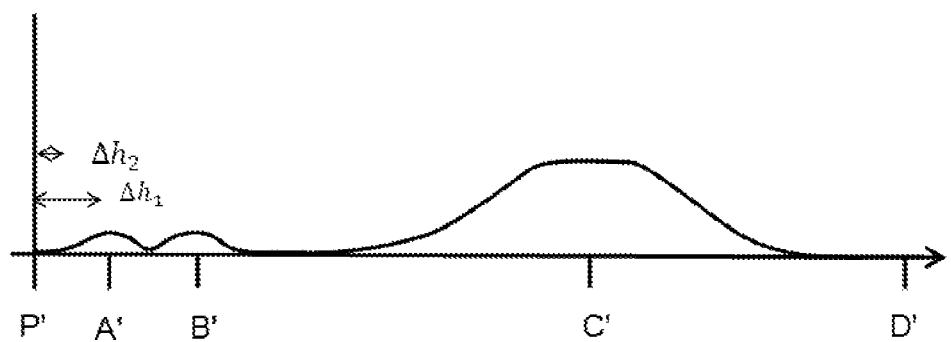
FIG. 2 illustrates a difference function depicting difference between the reference lumen and actual lumen of the blood vessel segment.

FIG. 2 is a diagram showing the geometrical parameter difference between the actual lumen and the reference lumen of FIG. 1 as a geometrical parameter difference function F(x). It is noted that, as revealed by an analysis, an accurate pressure deviation between a first blood flow pressure and a second blood flow pressure can be calculated using the geometrical parameter difference function F(x) in a single scale in the case of a single type of lesion. However, when multiple types of lesions, especially including a diffuse lesion, coexist in the blood vessel, the pressure deviation calculated by the method will suffer from a significant error. On the one hand, when the single scale is small, the derivative difference function at severe stenosis will be close to that at mild stenosis. This will lead to underestimation of the impact of the severe stenosis on the pressure deviation. On the other hand, when the single scale is great, the derivative of the difference function at the mild stenosis will be zero, i.e., failure to detect the impact of the mild stenosis on the pressure deviation.

In order to overcome the deficiencies of the conventional methods of a single scale, it is preferred to take derivative of the geometrical parameter difference in n scales for a blood vessel with different degrees of lesions, and calculate the pressure deviation between the first and second blood flow pressures based on derivative difference functions in these scales.

For example, in a preferred embodiment, derivative of the geometrical parameter difference function are derived in two scales, and the pressure deviation between the first and second blood flow pressures is calculated from there two scales of derivatives difference functions (including a first greater scale and a second smaller scale). The derivative difference function $f_1(x)$ in the first scale is adapted to detect a geometrical parameter difference between an actual lumen diameter and a reference lumen diameter caused by long severe lesion, with geometrical parameter differences caused by focal stenosis being ignored. The derivative difference function $f_2(x)$ in the second scale is adapted to detect a geometrical parameter difference caused by a focal change of the segment.

Derivatives of the difference function f(x) of FIG. 2 are taken in these two scales.

The derivative difference function in the greater scale is:

$$f_1(x) = \frac{F(X + \Delta h_1/2) - F(X - \Delta h_1/2)}{\Delta h_1},$$

and the derivative difference function in the smaller scale is:

$$f_2(x) = \frac{F(X + \Delta h_2/2) - F(X - + \Delta h_2/2)}{\Delta h_2}$$

where $\Delta h_1 > \Delta h_2$.

Figure 3A:
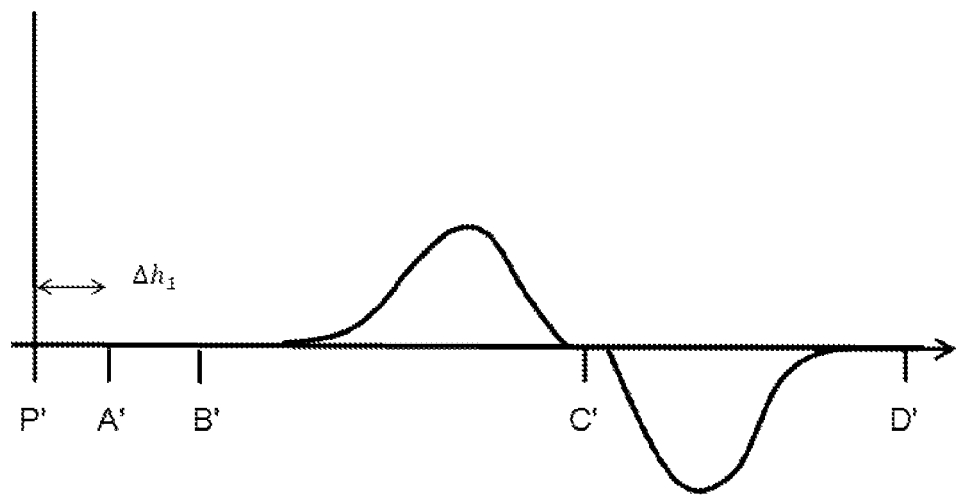
FIG. 3A is a diagram showing a derivative difference function $f_1(x)$ in a first scale.
Figure 3B:
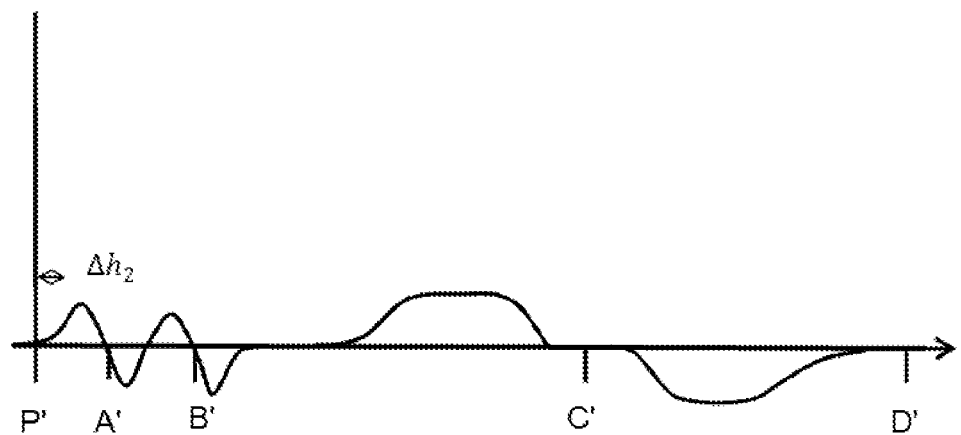
FIG. 3B is a diagram showing a derivative difference function $f_2(x)$ in a second scale.
Figure 4:
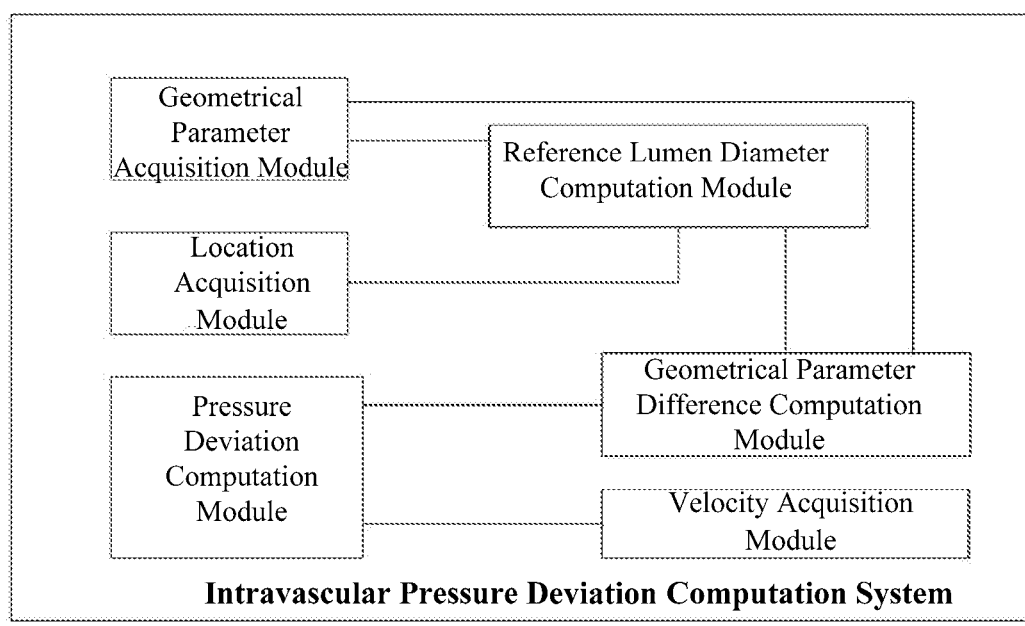
FIG. 4 is a schematic diagram of blood pressure drop system of the present invention.

As shown in FIGS. 3A and 3B, in the greater scale $\Delta h_1$, $F(X+\Delta h_1)-F(X)$ is nearly zero at focal lesion A, B. Therefore, $f_1(x)$ can reflect a geometrical parameter difference between an actual lumen diameter and a reference lumen diameter caused by long severe stenosis, with any geometrical parameter difference caused by focal stenosis being ignored. In the smaller scale $\Delta h_2$, geometrical parameter differences attributed to the focal stenosis A, B and the widely-affecting stenosis C can all be identified. However, according to the derivative difference function $f_2(x)$ in the smaller scale, the value of the derivatives for the different severity of stenosis are substantially equal and cannot be used to distinguish the different impacts of the stenosis on the pressure deviation. To achieve this, it is contemplated to weighting the derivative difference functions $f_1(x)$ and $f_2(x)$ in the two scales.

Embodiment 2

The present invention also provides a method for computing fractional flow reserve (FFR) of a segment of a blood vessel, comprising: receiving geometrical parameters of the segment comprising a proximal end and a distal end, the geometrical parameters comprising a first geometrical parameter representing a cross-sectional area (or diameter) of the segment at the proximal end, a second geometrical parameter representing a cross-sectional area (or diameter) of the segment at the distal end and a third geometrical parameter representing cross-sectional area (or diameter) at a first location between the proximal end and the distal end; with the proximal end point as a reference point, deriving a reference lumen diameter function and a geometrical parameter difference function based on the geometrical parameters and the distance from position along the segment to the reference point; obtaining derivatives the geometrical parameter difference function in multiple scales, wherein the scales are resolutions indicative of distances between two adjacent points when calculating derivative numerically; receiving a mean blood flow velocity of the segment obtained by conventional coronary angiography and obtaining a maximum mean blood flow velocity of the segment by looking up a table; and obtaining FFR as a ratio of a second blood flow pressure at the first location of the blood vessel to a first blood flow pressure at the proximal end of the segment, based on the multiple scales of derivative difference functions and the maximum mean blood flow velocity.

In a specific embodiment, the present invention provides a method for computing fractional flow reserve (FFR) of a segment of a blood vessel, comprising: obtaining a mean blood flow velocity V of the segment in a resting state optionally by conventional angiography (without maximum dilation of the microcirculation); calculating a maximum blood flow velocity $V_{max}$ at maximum dilation of microcirculation based on the mean velocity V; solving for a pressure deviation $\Delta P_{max}$ corresponding to the maximum blood flow velocity; and obtaining FFR according to equation FFR= (P1-$\Delta P_{max}$)/P1, where P1 represents a first blood flow pressure at the proximal end of the segment, which can be approximately estimated from the cardiac diastolic and systolic pressures or accurately measured using a catheter.

Preferably, the maximum blood flow velocity is obtained by looking up a correspondence table listing mean coronary blood flow velocities under a resting state and the corresponding maximum blood flow velocities at maximum dilation of microcirculation.

Preferably, the pressure deviation $\Delta P_{max}$ corresponding to the maximum blood flow velocity is obtained using the method of Embodiment 1.

Preferably, FFR may be computed for a given fixed maximum blood flow velocity $V_{max}$.

Embodiment 3

The present invention provides a system for computing a pressure deviation within a segment of a blood vessel, which can implement the method for computing a pressure deviation set forth in the foregoing embodiment. The system includes: a geometrical parameter data acquisition module, configured to acquire geometrical parameters of the segment, the blood vessel comprising a proximal end and a distal end, the geometrical parameters comprising a first geometrical parameter representing a cross-sectional area or diameter of the segment at the proximal end, a second geometrical parameter representing a cross-sectional area or diameter of the segment at the distal end and a third geometrical parameter representing a cross-sectional area or diameter of the segment at a first location between the proximal end and the distal end of the segment; a location data acquisition module, configured to acquire location data related to the first location; a velocity acquisition module, configured to acquire a mean blood flow velocity of the segment and the square of the mean blood flow velocity; a reference lumen diameter computation module, configured to a compute a reference lumen diameter at the first location of the blood vessel based on the first geometrical parameter, the second geometrical parameter, the third geometrical parameter and the location data related to the first location; a geometrical parameter difference computation module, configured to compute a geometrical parameter difference between the third geometrical parameter and the reference lumen diameter at the first location; and a pressure deviation computation module, configured to obtain the geometrical parameter difference data at the first location output from the geometrical parameter difference computation module and the mean blood flow velocity and its square from the velocity acquisition module and to compute the pressure deviation ΔP between a first blood flow pressure at the proximal end and a second blood flow pressure at the first location.

Preferably, the reference lumen diameter computation module is configured to derive a reference lumen diameter function, based on the first geometrical parameter, the second geometrical parameter and a distance x from a certain position along the segment of vessel to the proximal end as a reference point, wherein the reference lumen diameter function is used to represent reference lumen diameter along different positions along the blood vessel as a function of the distance x between the position and the reference point.

Preferably, the system further comprises a normalization module configured to preform linear normalization as a function of location from the proximal end to the distal end point of the vessel segment.

Preferably, the geometrical parameter difference computation module is configured to derive, with the proximal end point as a reference point, based on the third geometrical parameter and the reference lumen diameter function. The geometrical parameter difference function indicates a relationship of differences between the reference lumen diameter function and the received geometrical parameters with respect to the distances x from the reference point.

Preferably, the system further comprises a multi-scale derivative difference computation module configured to calculate derivatives of the geometrical parameter difference function in multiple scales. The pressure deviation computation module computes the pressure deviation ΔP between the first blood flow pressure and the second blood flow pressure by weighting integrals of the derivative difference functions in the multiple scales based on the output of the multi-scale difference derivative computation module as well as the mean blood flow velocity V and its square $V^2$ output from the velocity acquisition module.

The multiple scales comprise two or more scales implemented as resolutions indicative of distances between two adjacent points when calculating derivative The pressure deviation ΔP between the first blood flow pressure and the second blood flow pressure is computed based on multiple scales of derivatives difference function. The scales are resolutions indicative of distances between two adjacent points when calculating derivative numerically. The different scales comprise a first greater scale and a second smaller scale. The multiple scales of derivative difference functions comprise a first scale of derivative difference function $f_1(x)$ and a second scale of derivative difference function $f_2(x)$. Use of the multiple scales enables manifestation of different impacts of stenosis of different degrees of severity (focal and diffuse) in the segment on the pressure deviation. The first scale of derivative difference function $f_1(x)$ is adapted to detect a geometrical parameter difference between an actual lumen diameter and a reference lumen diameter caused by long severe stenosis, with geometrical parameter differences caused by focal stenosis being ignored. The second scale of derivative difference function $f_2(x)$ is adapted to detect a geometrical parameter difference between an actual lumen diameter and a reference lumen diameter caused by a focal change occurring in the stenotic segment.

In this case, the pressure deviation computation module computes the pressure deviation ΔP between the first blood flow pressure and the second blood flow pressure by weighting integrals of the first scale of derivative difference function $f_1(x)$ and the second scale of derivative difference function $f_2(x)$ output from the multi-scale difference derivative computation module and based on the mean blood flow velocity V and its square $V^2$ output from the velocity acquisition module.

Preferably, the pressure deviation computation module computes the pressure deviation ΔP between the first blood flow pressure and the second blood flow pressure according to $$\Delta P = \alpha[C_1V + C_2V^2]*\!\!\int\! f_1(x)dx + \beta[C_1V + C_2V^2]*\!\!\int\! f_2(x)dx$$

where $C_1$ and $C_2$ represent coefficients of the mean blood flow velocity V and its square $V^2$, respectively, and α and β denote weighting coefficients for the derivative difference functions in the first and second scales, respectively.

Preferably, in order to more accurately compute the pressure deviation in the segment of the blood vessel under various conditions, it is further contemplated to derive derivatives of the geometrical parameter difference function in n multiple scales and compute the pressure deviation ΔP between the first blood flow pressure and the second blood flow pressure based on the n scales of derivative difference functions. That is, the derivatives of the geometrical parameter difference function are calculated in the n scales, wherein the pressure deviation ΔP between the first blood flow pressure and the second blood flow pressure is computed based on the n scales of derivative difference functions. The scales are implemented as resolutions indicative of distances between two adjacent points when calculating derivative numerically. The n scales are a first scale, a second scale, . . . , and an n-th scale.

The derivative difference function $f_1(x)$ in the first scale is adapted to detect a geometrical parameter difference between an actual lumen diameter and a reference lumen diameter caused by a first lesion characteristic, with geometrical parameter differences caused by other lesions being ignored. The derivative difference function $f_2(x)$ in the second scale is adapted to detect a geometrical parameter difference between an actual lumen diameter and a reference lumen diameter caused by a second lesion characteristic, . . . , and the derivative difference function $f_n(x)$ in the n-th scale is adapted to detect a geometrical parameter difference between an actual lumen diameter and a reference lumen diameter caused by an n-th lesion characteristic, wherein n is a natural number greater than 1.

In this case, the pressure deviation computation module computes the pressure deviation ΔP between the first blood flow pressure and the second blood flow pressure according to $$\Delta P = \alpha_1[C_1V + C_2V^2]*\!\!\int\! f_1(x)dx + \alpha_2[C_1V + C_2V^2]\!\!\int\! f_2(x)dx + \ldots + \alpha_n[C_1V + C_2V^2]*\!\!\int\! f_n(x)dx$$

where, $C_1$ and $C_2$ represent coefficients for the mean blood flow velocity V and its square $V^2$, respectively, and $\alpha_1, \alpha_2, \ldots,$ and $\alpha_n$ denote weighting coefficients for the derivative difference functions $f_1(x), f_2(x), \ldots, f_n(x)$ in the n scales, respectively.

The location data related to the first location is a distance from the first location to the proximal end of the segment, and the mean blood flow velocity of the segment is a mean blood flow velocity between the proximal end and the distal end.

Preferably, the system further comprises a two-dimensional coronary angiography module configured to capture two-dimensional coronary angiography images of the segment under a certain angle and register region of interest of the images for different frame counts. The region of interest of the coronary angiography is from the proximal end of the segment to the distal end.

Preferably, the velocity acquisition module is configured to plot a gray-level histogram from the registered region of interest based on the output from the two-dimensional coronary angiography module, and to fit the gray-level histogram as a function of time within a cardiac cycle, based on which a mean flow velocity of contrast medium within the segment of the vessel are obtained.

Preferably, the mean blood flow velocity V within the segment is approximately equal to the mean flow velocity of the contrast medium.

Embodiment 4

The present invention provides a system for computing fractional flow reserve (FFR) of a segment of blood vessel, comprising: a geometrical parameter data acquisition module, configured to acquire geometrical parameters of the segment, the blood vessel comprising a proximal end and a distal end, the geometrical parameters comprising a first geometrical parameter representing a cross-sectional area (or diameter) of the segment at the proximal end, a second geometrical parameter representing a cross-sectional area (or diameter) of the segment at the distal end and a third geometrical parameter representing a cross-sectional area (or diameter) of the segment at a first location between the proximal end and the distal end; a location data acquisition module, configured to acquire location data related to the first location; a reference lumen diameter computation module, configured to derive, a reference lumen diameter function with respect to the distance from a certain position along the segment to the proximal end as a reference point; a geometrical parameter difference computation module, configured to derive a parameter difference function based on the reference lumen diameter function and the third geometrical parameter; a multi-scale computation module, configured to obtain derivatives of the geometrical parameter difference function in multiple scales implemented as resolutions indicative of distances between two adjacent points when calculating derivative numerically; a mean blood flow velocity acquisition module, configured to acquire a mean blood flow velocity of the segment through conventional coronary angiography; a maximum mean blood flow velocity computation module, configured to obtain a maximum mean blood flow velocity of the segment by looking up a correspondence table stored in the module; and an FFR computation module, configured to obtain FFR as ratio of a second blood flow pressure at the first location of the blood vessel to a first blood flow pressure at the proximal end, based on the multiple scales of derivative difference functions and the maximum mean blood flow velocity.

In a specific embodiment, the present invention also provides a system for computing fractional flow reserve (FFR) of a segment of a blood vessel, comprising: a mean blood flow velocity acquisition module, configured to acquire a mean blood flow velocity V of the segment preferably by conventional coronary angiography (without maximum dilation of microcirculation); a maximum blood flow velocity acquisition module, configured to calculate a maximum blood flow velocity $V_{max}$ under the condition of maximum dilation of microcirculation based on the mean velocity V; a pressure deviation computation module, configured to solve for a pressure deviation $\Delta P_{max}$ corresponding to the maximum blood flow velocity; and an FFR computation module, configured to obtain FFR, based on a first blood flow pressure at the proximal end of the blood vessel and the pressure deviation $\Delta P_{max}$, according to FFR= $(P1-\Delta P_{max})/P1$, wherein P1 can be approximately estimated from the cardiac diastolic and systolic pressures or accurately measured using a catheter.

The maximum blood flow velocity acquisition module may obtain the maximum blood flow velocity by looking up a correspondence table listing mean coronary blood flow velocities in a resting state and the corresponding maximum blood flow velocities under the condition of maximum dilation of myocardial microcirculation. The correspondence table may be stored on the maximum blood flow velocity acquisition module or another separate module of the system.

Preferably, the pressure deviation computation module may have the structure of the system of Embodiment 3 for obtaining the pressure deviation $\Delta P_{max}$ corresponding to the maximum blood flow velocity using the method of Embodiment 1.

Preferably, FFR may be computed for a given fixed maximum blood flow velocity $V_{max}$.

It is to be noted that the above systems and functional modules are presented merely as an example to describe a basic, but not the only, structure for implementing the present invention.

While the invention has been described with reference to several preferred embodiments, it is not intended to be limited to these embodiments in any sense. Various changes and modifications may be made by any person of skill in the art without departing from the spirit or scope of the invention. Accordingly, the scope of the invention shall be as defined in the appended claims.

The invention claimed is:

1. A method of detecting pressure deviation in a blood vessel segment, comprising:
   receiving geometrical parameters of a blood vessel segment comprising a proximal end and a distal end, wherein the geometrical parameters comprises a first geometrical parameter representing a cross-sectional area or diameter of the proximal end of the segment, a second geometrical parameter representing a cross-sectional area or diameter of the distal end of the segment, and a third geometrical parameter representing a cross-sectional area or diameter of the blood vessel segment at a first location between the proximal end and the distal end; wherein the geometrical parameters are obtained by two-dimensional or three-dimensional coronary angiography, coronary computed tomography angiography (CTA), intravascular ultrasound (IVUS) or optical coherence tomography (OCT);
   receiving a mean blood flow velocity of the blood vessel segment;
   with the proximal end point as a reference point, deriving a reference lumen diameter function based on the first geometrical parameter, the second geometrical parameter and a distance x from a certain position along the blood vessel segment to the reference point;
   wherein the reference lumen diameter function is used to represent reference lumen diameter at different positions along the blood vessel as a function of the distance x from the position to the reference point, and
   wherein the derivation of the reference lumen diameter function Preferably comprises a linear normalization as a function of location from the proximal end to the distal end of the segment;

with the proximal end point as a reference point, deriving a geometrical parameter difference function based on the third geometrical parameter and the reference lumen diameter function;

wherein the geometrical parameter difference function indicates a relationship of differences between the reference lumen diameter function and the received geometrical parameters with respect to the distances x from the reference point;

calculating derivatives of the geometrical parameter difference function in multiple scales, wherein the scales are resolutions indicative of distances between two adjacent points when calculating derivative numerically, wherein the multiple scales comprise a first greater scale and a second smaller scale, wherein the multiple scales of derivative difference functions comprise a derivative difference function $f_1(x)$ in the first scale and a derivative difference function $f_2(x)$ in the second scale, wherein use of the multiple scales enables manifestation of impacts of different severity of stenosis (focal and diffuse) on the pressure deviation;

wherein the derivative difference function $f_1(x)$ in the first scale is adapted to detect a geometrical parameter difference between an actual lumen diameter and a reference lumen diameter caused by stenosis affecting a wide range, with geometrical parameter differences caused by focal stenosis being ignored, wherein the derivative difference function $f_2(x)$ in the second scale is adapted to detect a geometrical parameter difference between an actual lumen diameter and a reference lumen diameter caused by a focal lesion; and obtaining a pressure deviation $\Delta P$ between a first blood flow pressure at the proximal end and a second blood flow pressure at the first location based on the derivatives of the geometrical parameter difference in multiple scales at the first location, the mean blood flow velocity V and a square of the mean blood flow velocity $V^2$.

2. The method of claim 1, further comprising: computing the pressure deviation $\Delta P$ between the first blood flow pressure and the second blood flow pressure by weighting integrals of the first scale of derivative difference function $f_1(x)$ and the second scale of derivative difference function $f_2(x)$ as well as the mean blood flow velocity V and its square $V^2$.

3. The method of claim 2, further comprising: computing the pressure deviation $\Delta P$ between the first blood flow pressure and the second blood flow pressure according to $$\Delta P = \alpha[C_1 V + C_2 V^2]*\int f_1(x)dx + \beta[C_1 V + C_2 V^2]*\int f_2(x)dx$$

where $C_1$ and $C_2$ represent coefficients of the mean blood flow velocity V and its square $V^2$, respectively, and $\alpha$ and $\beta$ denote weighting coefficients of the derivative difference functions in the first and second scales respectively.

4. The method of claim 1, further comprising:

computing derivatives of the geometrical parameter difference function in n scales, wherein the pressure deviation $\Delta P$ between the first blood flow pressure and the second blood flow pressure is computed based on the n scales of derivative difference functions, wherein the scales are resolutions indicative of distances between two adjacent points when calculating derivative numerically, wherein the n scales consist of a first scale, a second scale, . . . and an n-th scale, wherein the derivative difference function $f_1(x)$ in the first scale is adapted to detect a geometrical parameter difference between an actual lumen diameter and a reference lumen diameter caused by a first lesion characteristic, with geometrical parameter differences caused by other lesions being ignored, wherein the derivative difference function $f_2(x)$ in the second scale is adapted to detect a geometrical parameter difference between an actual lumen diameter and a reference lumen diameter caused by a second lesion characteristic, wherein the derivative difference function $f_n(x)$ in the n-th scale is adapted to detect a geometrical parameter difference between an actual lumen diameter and a reference lumen diameter caused by an n-th lesion characteristic, and wherein n is a natural number greater than 1.

5. The method of claim 4, further comprising:

computing the pressure deviation $\Delta P$ between the first blood flow pressure and the second blood flow pressure by weighting integrals of the n scales of derivative difference functions $f_1(x), \ldots, f_n(x)$ and the mean blood flow velocity V and the square of the mean blood flow velocity $V^2$.

6. The method of claim 5, further comprising: computing the pressure deviation $\Delta P$ between the first blood flow pressure and the second blood flow pressure according to $$\Delta P = \alpha_1[C_1 V + C_2 V^2]*\int f_1(x)dx + \alpha_2[C_1 V + C_2 V^2]*\int f_2(x)dx + \ldots + \alpha_n[C_1 V + C_2 V^2]*\int f_n(x)dx$$

where, $C_1$ and $C_2$ represent coefficients of the mean blood flow velocity V and its square $V^2$, respectively, and $\alpha_1, \alpha_2, \ldots,$ and $\alpha_n$ denote weighting coefficients for the derivative difference functions $f_1(x), f_2(x), \ldots, f_n(x)$ in the n scales, respectively.

7. The method of claim 1, wherein the location data related to the first location is a distance from the first location to the proximal end of the segment, and wherein the mean blood flow velocity is a mean velocity from the proximal end to the distal end.

8. The method of claim 1, further comprising: receiving two-dimensional coronary angiography images under a certain angle; and registering region of interest of the images for different frames, wherein the region of interest of the coronary angiography is from the proximal end point of the segment to the distal end.

9. The method of claim 8, further comprising: plotting a gray-level histogram from the registered region of interest and fitting the gray-level as a function of time within a cardiac cycle.

10. The method of claim 9, further comprising: obtaining a mean flow velocity of contrast medium within the segment from the gray-level fitting function.

11. The method of claim 10, wherein the mean blood flow velocity V of the blood vessel segment is approximately equal to the mean flow velocity of the contrast medium obtained from the gray-level fitting function.

* * * * *